United States Patent [19]

Botta

[11] 3,950,367

[45] Apr. 13, 1976

[54] PREPARATION OF N-CHLOROFORMYL-CARBAMIC ACID AMIDES AND ESTERS

[75] Inventor: Artur Botta, Krefeld, Germany

[73] Assignee: Bayer Aktiengesellschaft, Leverkusen, Germany

[22] Filed: Nov. 16, 1973

[21] Appl. No.: 416,569

[30] Foreign Application Priority Data

Nov. 22, 1972   Germany............................ 2257344

[52] U.S. Cl................. 260/455 A; 71/111; 71/107; 71/93; 71/94; 71/100; 71/119; 71/120; 71/76; 71/106; 71/112; 260/453 RW; 260/471 C; 260/482 C; 260/307 F; 260/544 C; 260/248 CS; 260/293.86

[51] Int. Cl.²..................................... C07C 155/02

[58] Field of Search........ 260/455 A, 482 C, 544 C, 260/471 C, 453 RW, 307 F, 248 CS, 293.86

[56] References Cited

UNITED STATES PATENTS

| | | | |
|---|---|---|---|
| 3,824,280 | 7/1974 | Kiefer et al. ..................... | 260/544 C |
| 3,829,482 | 8/1974 | Mueller et al................... | 260/482 C |
| 3,832,389 | 8/1974 | Koeing et al..................... | 260/479 C |

FOREIGN PATENTS OR APPLICATIONS

| | | | |
|---|---|---|---|
| 744,409 | 1/1970 | Belgium .......................... | 260/482 C |

Primary Examiner—Lewis Gotts
Assistant Examiner—D. R. Phillips
Attorney, Agent, or Firm—Burgess, Dinklage & Sprung

[57] ABSTRACT

N-Chloroformyl carbamic acid amides and esters having the functional group

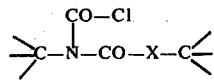

are prepared by reacting phosgene with an imino compound having the functional group

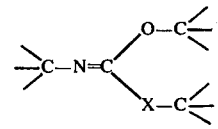

and free of interfering radicals. Preferably the starting material has the formula

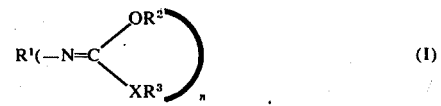

in which R¹ is a monovalent or divalent optionally substituted aliphatic, cycloaliphatic, araliphatic or aromatic radical, R² is an optionally substituted alkyl or aralkyl radical, R³ is a monovalent optionally substituted aliphatic, cycloaliphatic, araliphatic or aromatic radical, and any two of the radicals R¹, R² and R³ can conjointly be a constituent of a 4-membered to 7-membered heterocyclic ring, X is oxygen, sulfur or an N–R⁴ radical, in which R⁴ is an optionally substituted $C_1$–$C_6$ alkyl, cycloalkyl, aralkyl or aromatic radical, or R³ and R⁴ together optionally form a constituent of a 4-membered to 7-membered ring, and n is 1 when R¹ is monovalent and 2 when R¹ is divalent.

Certain of the compounds of the formula

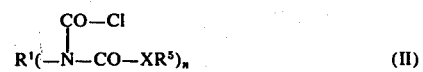

are new and herbicidally active.

8 Claims, No Drawings

PREPARATION OF N-CHLOROFORMYL-CARBAMIC ACID AMIDES AND ESTERS

It is known from German Published Specification DAS No. 1,259,871 to prepare N-chloroformylcarbamic acid esters by reaction of N-monoalkylcarbamic acid esters with phosgene in the presence of stoichiometric to excess amounts of tertiary amines. However, the conjoint use of a tertiary amine as an auxiliary base implies a considerable technical effort. N-Aryl-substituted or N-vinyl-substituted carbamic acid esters cannot be reacted with phosgene by this method.

Furthermore, some N-monochloroformyl-N,N'-dialkyl-ureas have already been prepared by phosgenation of the corresponding N,N'-dialkylureas. However, the smooth course of the reaction is restricted to some special cases and as a rule mixtures, which are difficult to separate, of N-phosgenation products (N-monochloroformylureas and/or isocyanates) and O-phosgenation products (chloroformamidinium chlorides) are produced. N-Aryl-ureas or N-vinyl-ureas cannot be reacted to give the corresponding N-chloroformylureas. This is discussed in "Neuere Methoden der praeparativen organischen Chemie" ("Recent Methods of Preparative Organic Chemistry"), Verlag Chemie, Weinheim/Bergstrasse, Volume VI, pages 211 et seq.

The present invention provides a process for the production of an N-chloroformyl-carbonic acid amide, i.e. an N-chloroformyl carbamic acid amide or ester having the functional group

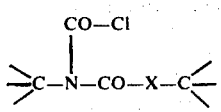

wherein X is oxygen, sulfur or

which comprises reacting an imino compound having the functional group

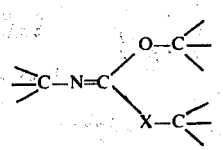

and free of interfering radicals with at least about 1 mole of phosgene per mole of imino group. Preferably the starting material has the formula

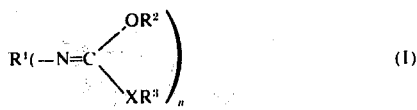

(I)

in which
  $R^1$ is a monovalent or divalent optionally substituted aliphatic, cycloaliphatic, araliphatic or aromatic radical,
  $R^2$ is an optionally substituted alkyl or aralkyl radical,
  $R^3$ is a monovalent optionally substituted aliphatic, cycloaliphatic, araliphatic or aromatic radical, and any two of the radicals $R^1$, $R^2$ and $R^3$ can conjointly be a constituent of a 4-membered to 7-membered heterocyclic ring,
  X is oxygen, sulfur or an N-$R^4$ radical, in which
  $R^4$ is an optionally substituted $C_1$-$C_6$ alkyl, cycloalkyl, aralkyl or aromatic radical, or
  $R^3$ and $R^4$ together optionally form a constituent of a 4-membered to 7 -membered ring, and
  $n$ is 1 when $R^1$ is monovalent and 2 when $R_1$ is divalent, and the reaction is effected at a temperature of about $-20°$ to $+200°C$.

Preferably, the reaction is carried out at from about $-10°$ to $+150°C$. The process of the invention is appropriately carried out with an excess of phosgene of about 0.1 to 1 mole per mole of imino group. Larger excesses are not detrimental.

As aliphatic radicals $R^1$, $R^2$ and $R^3$, there may be mentioned optionally substituted alkyl, alkenyl, alkylene and alkenylene radicals with up to about 22, preferably up to about 18, and especially up to about 8, carbon atoms. Possible optionally substituted cycloaliphatic radicals include polycyclic radicals, for example the decalyl radical, but cycloalkyl, cycloalkenyl, cycloalkylene and cycloalkenylene with about 4 to 10, preferably 5 or 6, carbon atoms are preferred.

Suitable optionally substituted araliphatic radicals contain 1 to about 4, preferably 1 or 2, carbon atoms in the aliphatic chain, and contain a naphthyl or phenyl radical, preferably a phenyl radical, as the optionally substituted aromatic moiety. Suitable optionally substituted aromatic radicals $R^1$ and $R^3$ contain up to about 14 carbon atoms in the ring system and are preferably naphthyl, naphthylene, phenyl or phenylene, it also being possible for two or more aromatic radicals to be linked through C—C bonds or via bridge members, such as oxygen, sulfur, $SO_2$, $CH_2$ or an isopropylidene radical, e.g. radicals of diphenyl, diphenylether, diphenylthioether, diphenylsulfone, diphenylmethane, dimethyl-diphenylmethane, and the like.

As alkyl radicals $R^4$ there may be mentioned those with 1 to about 6, preferably 1 to about 4, carbon atoms; the preferred cycloalkyl radicals are those with 5 or 6 carbon atoms in the ring system; the preferred aralkyl radical is the benzyl radical; and the preferred aromatic radical is the phenyl radical.

As preferred substituents of the radicals $R^1$, $R^2$ $R^3$ and $R^4$ there may be mentioned: alkyl radicals with 1 to about 4, preferably 1 or 2, carbon atoms, halogen (preferably fluorine, chlorine or bromine), nitrile, nitro (usually to a maximum of two such groups), alkoxy and alkylmercapto radicals, each with 1 to about 4 carbon atoms, aryloxy and arylmercapto groups (preferably phenyloxy and phenylmercapto), $C_1$-$C_6$ alkoxycarbonyl radicals (preferably methoxycarbonyl and ethoxycarbonyl), aryloxycarbonyl (preferably phenoxycarbonyl), $C_1$-$C_6$ acyloxy radicals (preferably acetoxy), benzoyloxy, alkylsulfonyl radicals with 1 to about 4 carbon atoms in the alkyl moiety, and arylsulfonyl radicals (preferably phenylsulfonyl and tolylsulfonyl). Particularly preferred substitutents are the halogens, nitrile, nitro, alkoxy, alkylmercapto and alkoxycarbonyl. Of course, it is possible for a radical to bear more than one substituent, the substituents being then alike or different.

The starting compounds used for the process of the invention are known or are obtainable according to known methods (Angewandte Chemie 81, 18, 1969). The following may be mentioned as examples of compounds that can be used for the process: methyl-, ethyl-, propyl-, isopropyl-, n-butyl-, isobutyl-, tert.butyl-, hexyl-, octyl-, dodecyl-, stearyl-, cyclobutyl-, cyclopentyl-, cyclohexyl-, methylcyclohexyl-, cyclooctyl-, vinyl-, allyl-, propenyl-, isopropenyl-, butenyl-, butynyl-, hexenyl-, undecenyl-, cyclopentenyl-, cyclohexenyl-, trifluoromethyl-, trichloromethyl-, chloroethyl-, bromoethyl-, pentafluoroethyl-, pentachloroethyl-, chloroisobutyl-, chlorocyclohexyl-, chlorovinyl-, dichlorovinyl-, trichlorovinyl-, chloropropenyl-, chlorocyclohexenyl-, cyanoethyl-, cyanopentyl-, methoxyethyl-, phenoxyethyl-, ethylmercaptopropyl-, ethoxycarbonylpentyl-, methylsulfonylhexyl-, benzyl-, phenethyl-, α,α-dimethylbenzyl-, p-chlorobenzyl-, m-nitrobenzyl-, p-ethoxycarbonylbenzyl-, m-cyanophenethyl-, phenyl-, o-, m- and p-tolyl-, isopropylphenyl-, tert.-butylphenyl-, fluorophenyl-, chlorophenyl-, bromophenyl-, trifluoromethylphenyl-, trichloromethylphenyl-, nitrophenyl-, cyanophenyl-, methoxyphenyl-, butylmercaptophenyl-, phenylmercaptophenyl-, methoxycarbonylphenyl-, acetoxyphenyl-, benzoylmercaptophenyl-, p-octylphenyl-, dichlorophenyl-, trichlorophenyl-, pentachlorophenyl-, 3,5-dinitrophenyl-, o-methyl-p-nitrophenyl-, o-chloro-m-nitrophenyl-, m-ethoxycarbonylphenyl-, p-benzoylphenyl-, p-benzenesulfonyl-, p-chlorodiphenyl-, naphthyl-(1) and -(2), chloronaphthyl-, nitronaphthyl-, ethylene-bis-, isopropylidene-bis-, propylene-1,2-bis-, propylene-1,3-bis-, butylene-1,4-bis-, pentylene-bis-, hexylene-bis-, decamethylene-bis-, dodecamethylene-bis-, cyclohexylene-1,4-bis-, o-, m- and p-phenylene-bis, methylphenylene-bis-, dichlorophenylene-bis-, trichloromethylphenylene-bis-, cyanophenylene-bis-, nitrophenylene-bis-, p,p'-diphenylene-bis-, p,p'-iso-propylidene-diphenylene-bis-, diphenyl-ether-p,p'-bis-, diphenylsulfide-p,p'-bis-, diphenylsulfone-p,p'-bis- or napthylene-1,4-bis-imino-dimethylcarbonate and the corresponding -imino-diethyl-carbonate, -iminodipropylcarbonate, iminodiisopropylcarbonate, -iminodibutylcarbonate, -imino-dihexylcarbonate, -imino-dioctylcarbonate, -imino-dibenzyl-carbonate, -imino-methyl-ethyl-carbonate, -imino-methyl-butyl-carbonate, -imino-ethyl-benzyl-carbonate, -imino-methyl-, octylcarbonate, -imino-propyl-decylcarbonate, -imino-methyl-stearylcarbonate, imino-methyl-phenyl-carbonate, -imino-ethyl-chlorophenyl-carbonate, -imino-propyl-nitrophenyl-carbonate, -imino-benzyl-methoxyphenyl-carbonate, -imino-methyl-methylthiol-carbonate, -imino-benzyl-butylthiol-carbonate, -imino-ethyl-phenylthiol-carbonate, -imino-butyl-p-methyl-phenylthiol-carbonate, -imino-ethylenecarbonate, -imino-propylene-1,2-carbonate, -imino-butylene-2,3-carbonate, -imino-propylene-1,3-carbonate, imino-butylene-1,4-carbonate, -imino-phenylethylenecarbonate, -imino-ethylene-monothiolcarbonate, -imino-propylene-1,3-monothiolcarbonate, -imino-butylene-1,4-monothiolcarbonate, -imino-dimethylcarbamic acid methyl ester, -imino-diethylcarbamic acid ethyl ester, -imino-dibutylcarbamic acid benzyl ester, - imino-piperididocarbamic acid methyl ester, -imino-phenyl-methylcarbamic acid propyl ester, -imino-diphenylcarbamic acid butyl ester, -imino-N-methyloxazolidone-2, -imino-N-cyclohexyloxazolidone-2, -imino-N-phenyloxazolidone-2, -imino-N-ethyl-tetrahydrooxazinone-2 and -imino-N-isopropyl-hexahydro-1,3-oxazepinone-2; 2-methoxy-, 2-ethoxy-, 2-propyloxy-, 2-decyloxy-, 2-cyclohexyloxy-, 2-benzyloxy-, 2-phenyloxy-, 2-chlorophenoxy-, 2-nitrophenoxy-, 2-methoxyphenyloxy-, 2-cyanophenoxy-, 2-methylmercapto-, 2-butylmercapto-, 2-phenylmercapto-, 2-p-chlorophenylmercapto-, 2-dimethylamino-, 2-diethylamino-, 2-piperidido-, 2-morpholino-, 2-methylphenyl-amino- or 2-diphenylamino-Δ²-oxazoline and the corresponding -Δ²-4,4-dimethyloxazoline, Δ²-4,5-dimethyloxazoline, -Δ²-dihydro-1,3-oxazine and -Δ²-tetrahydro-1,3-oxazepine; and 2-methoxy-, 2-ethoxy-, 2-tert.-butoxy-, 2-allyloxy- or 2-benzyloxy-Δ²-thiazoline and the corresponding -Δ²-4,4-diethyl-thiazoline, -Δ²-hexahydrobenzthiazole, -Δ²-dihydro-1,3-thiazine, -Δ²-tetrahydro-1,3-thiazepine, -Δ²-1-methyl-imidazoline, -Δ²-1-phenyl-imidazoline, -Δ²-1-benzyl-imidazoline, -Δ²-1-ethyl-tetrahydropyrimidine and -Δ²-1-methyl-tetrahydro-1,3-diazepine.

The process according to the invention may be illustrated by the following equations:

(a)

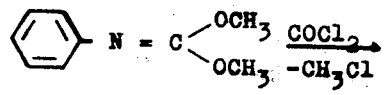

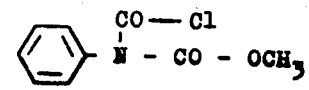

(1)

(b)

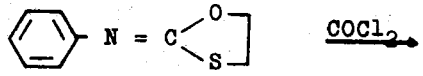

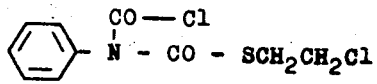

(6)

(c)

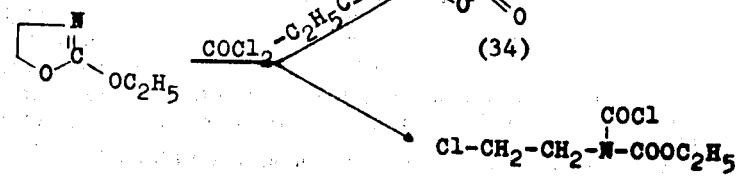

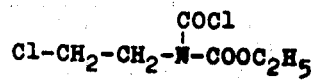

(d)

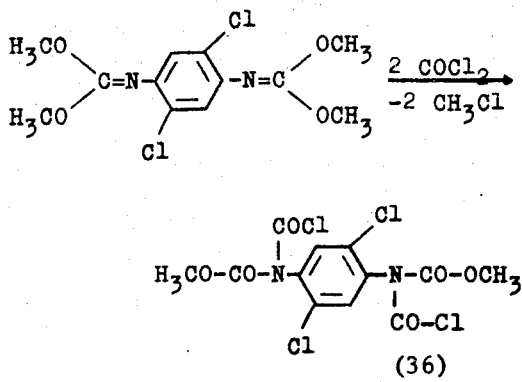

(36)

The compounds obtainable according to the process of the invention correspond to the general formula

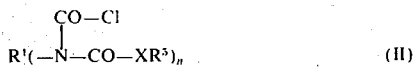

in which
R¹, X and n have the above-mentioned meanings, and
R⁵ has the range of meanings stated above for R³ or, if R² and R³ are constituents of a ring system,
R⁵ is an ω-chloroalkyl radical which contains the carbon chain originally belonging to R² and R³, or
R¹ and R⁵ conjointly form a constituent of a 4-membered to 7-membered heterocyclic ring.

The new compounds obtainable according to the process of the invention correspond to the above-mentioned formula (II) wherein the radicals R¹ and R⁵ as well as the integer n having the above-mentioned meanings if X represents sulfur; or R¹ is an optionally substituted aromatic radical, in which case n is 1 or 2; or R¹ is a Δ¹-alkenyl radical, for example the vinyl or chlorovinyl radical, in which case n is 1, X can be oxygen or the radical NR⁴, with R⁴ having the above-mentioned meaning, and R⁵ having the above-mentioned range of meanings.

A significant class of the new compounds are those of the above formula (II)
in which, if X is sulfur, R¹ is a monovalent or divalent aliphatic radical with up to about 22 carbon atoms, a cycloaliphatic radical with about 5 or 6 carbon atoms, an araliphatic radical with 1 to about 4 carbon atoms in the aliphatic chain and phenyl or naphthyl as the aromatic radical, or an aromatic radical with up to about 14 carbon atoms in the ring system, it being possible for two or more aromatic radicals to be linked through C—C bonds or via bridge members, such as oxygen, sulfur, $SO_2$, $CH_3$ or an isopropylidene radical, the above-mentioned radicals optionally being substituted by halogen, nitrile, nitro, or alkoxy, alkylmercapto or alkoxycarbonyl with up to about 4 carbon atoms in each alkyl moiety, R⁵ is a monovalent radical having the foregoing range of meanings given for R¹ or is an ω-chloroalkyl radical with 2 to about 6 carbon atoms, and n is 1 when R¹ is monovalent radical and 2 when R¹ is divalent, or in which, if X is oxygen or an NR⁴ radical, R¹ is furthermore a Δ¹-alkenyl radical, such as vinyl, isopropenyl, monochlorovinyl, dichlorovinyl, trichlorovinyl or chloroisopropenyl, and n is 1, or R¹ is furthermore an aromatic radical with up to about 14 carbon atoms in the ring system, it being possible for two or more aromatic radicals to be linked through C—C bonds or via bridge members, such as oxygen, sulfur, $SO_2$, $CH_2$ or an isopropylidene radical, the above-mentioned radicals optionally being substituted by halogen, nitrile, nitro, or alkoxy, alkylmercapto or alkoxycarbonyl with up to about 4 carbon atoms in each alkyl moiety, and n is 1 when R¹ is monovalent and 2 when R¹ is divalent, R⁵ has the above-mentioned range of meanings, and R⁴ is an alkyl radical of 1 to about 4 carbon atoms, a cyclopentyl or cyclohexyl radical, a benzyl radical or a phenyl radical, the radicals mentioned being optionally substituted by halogen, nitrile, nitro, or alkoxy, alkylmercapto or alkoxycarbonyl with up to about 4 carbon atoms in each alkyl moiety.

In preferred new compounds of the formula (II), if X is sulfur, then R¹ is an optionally substituted, alkyl, alkenyl, alkylene or alkenylene radical with up to 18, especially up to about 8, carbon atoms, an optionally substituted cycloalkyl, cycloalkenyl, cycloalkylene or cycloalkenylene radical with 4 to 10, especially 5 or 6, carbon atoms in the ring, an optionally substituted benzyl, phenethyl or xylylene radical or an optionally substituted phenyl, naphthyl, phenylene or naphthylene radical, and, if X is oxygen or an NR⁴ group, is furthermore an optionally substituted phenyl, naphthyl, phenylene or naphthylene radical or a vinyl, Δ¹-propenyl or isopropenyl radical or a chlorine substitution product thereof, with R⁴ (if present) being alkyl with 1 to about 4 carbon atoms, cyclohexyl or an optionally substituted benzyl or phenyl radical, while the radical R⁵ is optionally substituted alkyl or alkenyl with up to 18, especially up to about 8, carbon atoms, optionally substituted cycloalkyl or cycloalkenyl with 4 to 10, especially 5 or 6, carbon atoms, optionally substituted benzyl or phenethyl or optionally substituted phenyl or naphthyl, or, if R² and R³ in the starting material were a constituent of a ring, β-chloroethyl, β-chloropropyl, γ-chloropropyl, β-chloroisobutyl or β-chlorotertiary butyl.

Possible substituents of the above-mentioned radicals are alkyl radicals with 1 to 4, preferably 1 or 2, carbon atoms, halogen (preferably fluorine, chlorine or bromine), nitrile, nitro (usually to a maximum of two such groups), alkoxy and alkylmercapto radicals, each with 1 to 4 carbon atoms, aryloxy and arylmercapto groups (preferably phenyloxy and phenylmercapto), $C_1$–$C_6$ alkoxycarbonyl radicals (preferably methoxycarbonyl and ethoxycarbonyl), aryloxycarbonyl (preferably phenoxycarbonyl), $C_1$–$C_6$ acyloxy radicals (preferably acetoxy), benzoyloxy, alkylsulfonyl radicals with 1 to 4 carbon atoms in the alkyl moiety, and arylsulfonyl radicals (preferably phenylsulfonyl and tolylsulfonyl).

Especially preferred new compounds of the formula (II) contain, as substituents of the last-mentioned radicals R¹ and R⁵, alkyl with 1 or 2 carbon atoms, fluorine, chlorine, bromine, nitrile, nitro, $C_1$–$C_4$ alkoxy, $C_1$–$C_4$ alkylmercapto, methoxycarbonyl or ethoxycarbonyl.

Examples of preferred new compounds are N-chloroformyl-phenylcarbamic acid methyl-, butyl- or phenylthiol ester, N-chloroformyl-3,4-dichlorophenylcarbamic acid methyl ester, N-chloroformylphenylcarbamic acid β-chloroethyl(thiol) ester, N-chloroformyl-vinylcarbamic acid methyl ester, N-chloroformyl-(cis- or trans-β-chlorovinyl)-carbamic acid methyl ester, N-chloroformyl-N-chloroformyl-N-phenyl-N′,N′-pentamethyleneurea and N-chloroformyl-N-phenyl-N′-(β-chloroethyl)-N′-methylurea.

During the phosgenation reaction, in the case of linear starting compounds, the radical $R^2$ is eliminated as $R^2Cl$ from the trunk molecule. If, on the other hand, in the case of cyclic compounds, $R^2$ forms a ring with $R^1$ or with $R^3$, $R^2$ remains, after splitting of the $OR^2$ bond, together with one of the radicals $R^1$ or $R^3$ in the molecule as an ω-chloroalkyl group.

In view of the state of the art, the fact that the process of the invention can be carried out must be regarded as distinctly surprising. A considerable advantage of the process of the invention is that the phosgenation reaction makes it superfluous to use a tertiary amine as an auxiliary base. Although the process of the invention can also be carried out in the absence of diluents, it is appropriately carried out in the presence of an inert solvent. Representative examples of such solvents are hydrocarbons, such as hexane, cyclohexane, ligroin, benzene, toluene, xylenes, cumene and decalin; halogenated hydrocarbons, such as methylene chloride, chloroform, carbon tetrachloride, trichloroethylene, dichloropropane, chlorobenzene, dichlorobenzene and chloronaphthalene; nitrohydrocarbons, such as nitromethane, nitropropane and nitrobenzene; ethers, such as diethyl ether, dioxane or anisole; esters, such as ethyl acetate, butyl acetate or methylglycolether acetate; and their mixtures.

The process according to the invention can be carried out under normal or elevated pressure, continuously or discontinuously.

In general, the procedure followed in carrying out the process of the invention is to introduce phosgene into a solution or suspension of the starting compound in an inert solvent or diluent, if appropriate while cooling, or to introduce the solution or suspension of the imino compound into a solution of phosgene in an inert solvent. Depending on the reactivity of the starting materials used, the reaction mixture is brought to the desired reaction temperature, if appropriate while passing in further phosgene, and after completion of the reaction mixture is worked up in the usual manner, if appropriate by distillation. The compounds obtainable according to the process are purified by distillation, optionally under reduced pressure, and/or by recrystallization.

The compounds obtainable according to the process of the invention, including the new compounds, are valuable intermediates for the production of plant-protection agents. They can also be employed directly as herbicides (see DOS No. 2,115,096). The compounds produced according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional herbicide formulations or compositions, e.g. conventional herbicide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional herbicide dispersible liquid diluent carriers and/or dispersible solid carriers optionally with the use of carrier vehicle assistants, e.g. conventional herbicide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other herbicides, or insecticides, acaricides, fungicides, bactericides, rodenticides, nematocides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95 percent by weight, and preferably 0.5–90 percent by weight, of the mixture, whereas carrier composition mixtures suitable for direct application or field application generally contemplate those in which the active compound is present in an amount substantially between about 0.0001–10 percent, preferably 0.01–1 percent, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95 percent, and preferably 0.01–95 percent, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95 percent by weight of the active compound or even the 100 percent active substance alone, e.g. about 20–100 percent by weight of the active compound.

Furthermore, the present invention contemplates methods of selectively killing, combating or controlling unwanted vegetation which comprises applying to at least one of correspondingly (a) such unwanted vegetation, and (b) the corresponding habitat thereof, i.e. the locus to be protected, a correspondingly combative or toxic amount, i.e. a herbicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The process of this invention is illustrated in the following preparative Examples.

EXAMPLE 1

A solution of 83 g (0.5 mole) of phenyliminocarbonic acid dimethyl ester in 100 ml of chlorobenzene was allowed to run into a solution of 50 g of phosgene in 400 ml of chlorobenzene at 0°C, while stirring and cooling, and the reaction mixture was then gradually brought to the reflux while introducing a further 50 g of phosgene. The mixture was kept at 130°C for a further hour, excess phosgene was expelled with nitrogen, the mixture was concentrated under reduced pressure and the residue which remained was recrystallized from 2–3 parts by weight of toluene. The yield of N-chloroformyl-phenyl-carbamic acid methyl ester of the formula

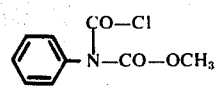

was 95.5 g (89.5 percent of theory) of colorless crystals of melting point 128°C and boiling point 150°–153°C/12 mm Hg.

EXAMPLE 2

A solution of 85.6 g (0.5 mole) of cyclohexyliminocarbonic acid dimethyl ester in 100 ml of toluene was run into a solution of 50 g of phosgene in 400 ml of toluene while stirring and cooling at −10°C. The temperature was then gradually brought to 110°C while introducing a further 50 g of phosgene and the mixture was additionally kept under reflux for 1 hour. After expelling excess phosgene with nitrogen, the mixture was concentrated under reduced pressure and the residual oil was distilled off in vacuo. 90 g (82 percent of theory) of N-chloroformyl-cyclohexylcarbamic acid methyl ester of the formula

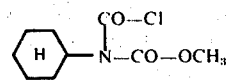

were obtained as a colorless oil of boiling point 65°–68°C/0.1 mm Hg.

EXAMPLE 3

A total of 75 g of phosgene was introduced into a solution of 48.3 g (0.25 mole) of phenyliminocarbonic acid diethyl ester in 400 ml of toluene over the course of 1½ hours, starting at 0°C and gradually raising the temperature to 110°C. The mixture was additionally kept at the reflux temperature for 1 hour, residual phosgene was expelled with dry nitrogen, the solution was concentrated under reduced pressure and the residue which remained was recrystallized from cyclohexane. The yield of N-chloroformyl-phenylcarbamic acid ethyl ester of the formula

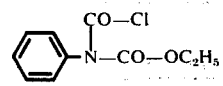

was 53 g (93 percent of theory) of colorless crystals of melting point 86°C.

EXAMPLE 4

20 g of phosgene were initially introduced at 0°C into a solution of 43.7g (0.2 mole) of N-phenyl-N′,N′-pentamethylene-O-methyl-isourea in 400 ml of methylene chloride. A further 20 g of phosgene were then introduced at the reflux temperature, the mixture was then kept at 40°C for 2 hours, excess phosgene was expelled with nitrogen and the residue was concentrated, initially under normal pressure and finally in vacuo. After recrystallizing the residue which remained from 2 parts by weight of benzene, 51 g (95.7 percent of theory) of N-chloroformyl-N-phenyl-N′-N′-pentamethyleneurea of the formula

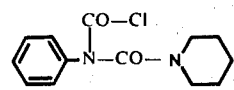

were obtained as colorless crystals of melting point 83°C.

EXAMPLE 5

A total of 50 g of phosgene was introduced into a solution of 44 g (0.25 mole) of 3-methyl-2-phenyliminooxazolidone-(2) in 400 ml of $CH_2Cl_2$, starting at −5°C and gradually raising the temperature to 40°C. The mixture was kept at the reflux temperature for a further 2 hours and excess phosgene was expelled by passing dry nitrogen through the mixture.

After removing the solvent, initially under normal pressure and finally in vacuo, N-chloroformyl-N-phenyl-N'-(β-chloroethyl)-N'-methylurea of the formula

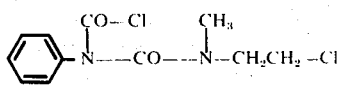

was left as a light viscous oil: 69 g (100 percent of theory). The compound was sufficiently pure for further reactions:
Cl calculated: 25.75% found: 25.5%

EXAMPLE 6

A total of 50 g of phosgene was introduced into a solution of 35.8 g (0.2 mole) of phenyliminocarbonic acid ethylene-monothiol ester in 300 ml of methylene chloride, starting at −5°C and gradually raising the temperature to 40°C. The mixture was kept at 40°C for a further 3 hours, excess phosgene was expelled with nitrogen and residual phosgene together with the solvent was stripped off, initially under normal pressure and subsequently in a water-pump vacuum. The crystalline residue from concentrating the mixture was recrystallized from 2 parts by weight of cyclohexane. The yield of N-chloroformyl-phenylcarbamic acid β-chloroethylthiol ester of the formula

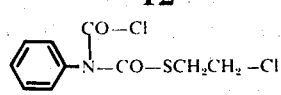

was 45 g (82 percent of theory) of colorless crystals of melting point 92°C and boiling point 163°–165°C/0.3 mm Hg.

EXAMPLE 7

30 g of phosgene were introduced into a solution of 23 g (0.1 mole) of n-butylamino-carbonic acid dibutyl ester in 300 ml of o-dichlorobenzene over the cource of 1½ hours, starting at 20°C and gradually raising the reaction temperature to 150°C. The mixture was kept at 150°C for a further 1½ hours, excess phosgene was expelled with nitrogen, the mixture was concentrated in a water-pump vacuum and the residue which remained was distilled in vacuo. The yield of N-chloroformyl-butylcarbamic acid butyl ester of the formula

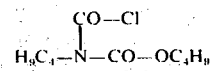

was 20.5 g (87 percent of theory) of a colorless oil of boiling point 84° – 85°c/0.2 mm Hg.

The following compounds were also produced by methods analogous to those described above.

| Ex. No. | Starting material | End Product | Procedure analogous to Example | Boiling point, °C/mm Hg or melting point °C |
|---|---|---|---|---|
| 8 | H₃C—C(CH₃)(CH₃)—N(OCH₃)(OCH₃) | H₃C—C(CH₃)(CH₃)—N(CO—Cl)(CO—OCH₃) | 2 | Boiling point: 90/11 |
| 9 | ClCH₂—CH(CH₃)—N(OCH₃)(OCH₃) | ClCH₂—CH(CH₃)—N(CO—Cl)(CO—OCH₃) | 1 | Boiling point: 106 – 109/12 |
| 10 | 2-Cl-cyclohexyl-N(OCH₃)(OCH₃) | 2-Cl-cyclohexyl-N(CO-Cl)(CO-OCH₃) | 1 | Boiling point: 105 – 106/0.1 |
| 11 | CH₂=CH—N(OCH₃)(OCH₃) | CH₂=CH—N(CO—Cl)(CO—OCH₃) | 6 | Boiling point: 43 – 46/0.15 |
| 12 | (H)(Cl)C=C(H)—N(OCH₃)(OCH₃) (cis) | (H)(Cl)C=C(H)—N(CO—OCH₃)(CO—Cl) | 7 | Boiling point: 72 – 74/0.25 |
| 13 | (Cl)(H)C=C(H)—N(OCH₃)(OCH₃) (trans) | (Cl)(H)C=C(H)—N(CO—OCH₃)(CO—Cl) | 7 | Boiling point: 79 – 80/0.15 |
| 14 | C₆H₅—N(OCH₃)(OC₄H₉) | C₆H₅—N(CO—Cl)(CO—OC₄H₉) | 4 | Boiling point: 108/0.01 |
| 15 | C₆H₅—N(OC₈H₁₇)(OC₈H₁₇) | C₆H₅—N(CO—Cl)(CO—OC₈H₁₇) | 7 | Boiling point: 163 – 164/0.3 |

-continued
| Ex. No. | Starting material | End Product | Procedure analogous to Example | Boiling point, °C/mm Hg or melting point °C |
|---|---|---|---|---|
| 16 | 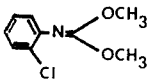 | 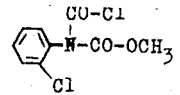 | 4 | Melting point: 71 |
| 17 | 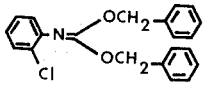 | 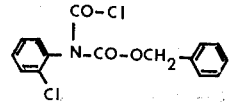 | 7 | Boiling point: (decomposition) 175 – 177/0.8 |
| 18 | 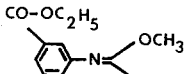 | 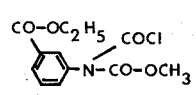 | 4 | Melting point: 83 |
| 19 | 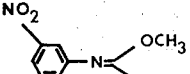 | 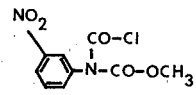 | 4 | Melting point: 112 |
| 20 | 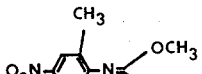 | 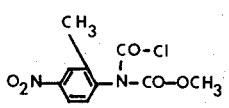 | 4 | Melting point: 108 |
| 21 | 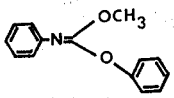 | 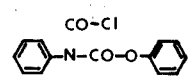 | 3 | Melting point: 120 |
| 22 | 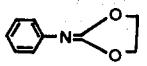 | 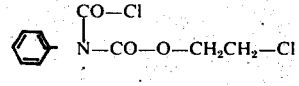 | 6 | Boiling point: 143 – 145/0.2 |
| 23 | 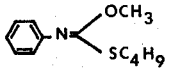 | 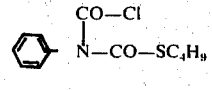 | 1 | Boiling point: 134 – 135/0.1 |
| 24 | 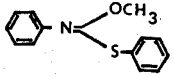 | 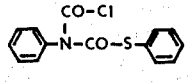 | 1 | Boiling point: 152 – 154/0.1 Melting point: 80 |
| 25 | 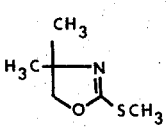 | 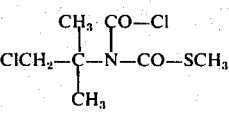 | 3 | Boiling point: 95 – 97/0.3 |
| 26 | 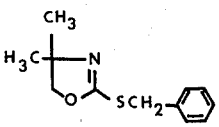 | 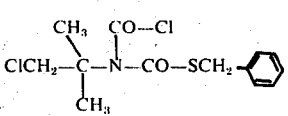 | 3 | Boiling point: (115 – 130/0.5) decomposition. |

-continued
| Ex. No. | Starting material | End Product | Procedure analogous to Example | Boiling point, °C/mm Hg or melting point °C |
|---|---|---|---|---|
| 27 | 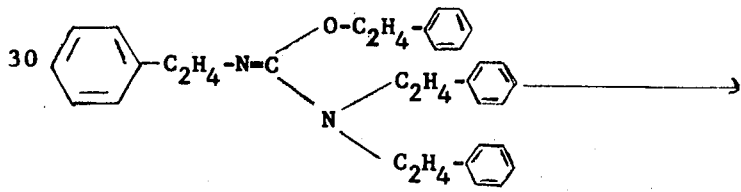 | | 1 and 4 | Boiling point: 125 – 128/0.5 |
| 28 | | | 5 | Viscous oil |
| 29 | 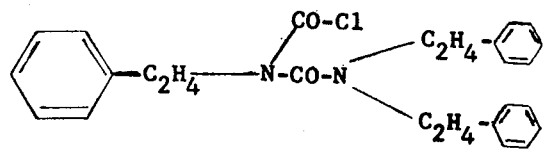 | | 7 | Boiling point: 193 – 197/0.5 Melting point: 148 |
Other compounds which may be similarly reacted to give the indicated end products include
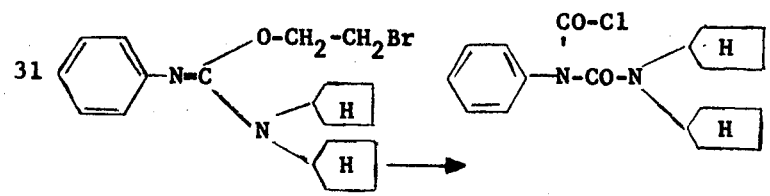
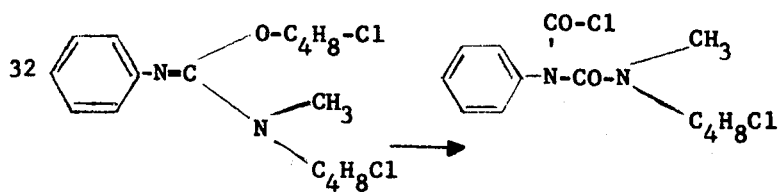

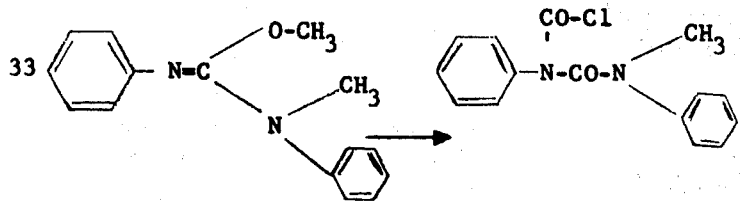

Le A 14 693

It will be appreciated that the instant specification and examples are set forth by way of illustration and not limitation, and that various modifications and changes may be made without departing from the spirit and scope of the present invention.

Hereinbelow is given an example for the conversion of a compound (A) of the general formula (II) to a herbicidally active tetrahydro-1.3.5-triazin-2.6-dione derivative (D):

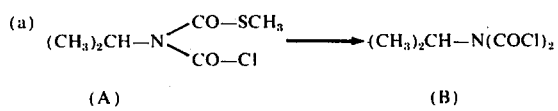

0.1 mole of N-chlorocarbonyl-isopropylcarbamic acid methylthiole ester were dissolved in 100 ml of carbon tetrachloride and, at 25°C, 0,3 mole of chlorine were introduced. The reaction took place exothermally. Thereafter the solvent and the sulfur chlorides formed during the reaction were removed in vacuo; the residue was distilled in vacuo.

N-isopropyl-bis-(chlorocarbonyl)-amine (B) was obtained as a pale yellow liquid (85% yield).

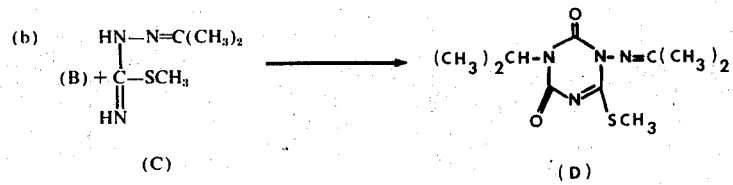

0,1 mole of N-isopropyl-bis-(chlorocarbonyl)-amine (B) were dissolved in 100 ml of benzene. The solution was stirred vigorously and a suspension of 0,1 mole of acetone-S-methylisothio-semicarbazone hydroiodide (C) in 100 ml of benzene was added. Then a solution of 0,2 mole of triethyl amine in 50 ml of benzene was added dropwise. The reaction mixture was stirred for a further hour, and the precipitate was filtered off. The precipitate was then treated with 100 ml of chloroform and 100 ml of water. The chloroform phase was separated off, dried with calcium chloride and, together with the benzene phase, concentrated in vacuo. The residue was recrystallized from isopropanol.

1-isopropyl-3-isopropylideneamino-4-methylmercapto-tetrahydro-1.3.5-triazine-2.6-dione (D) was obtained as a pale yellow solid of melting point 110°-112°C (75% yield).

The herbicidal activity of compound (D) is shown in the following tests:

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants, which had a height of 5–15 cm, were sprayed with the preparation of the active compound in such a way that the amounts of active compound per unit area shown in the table were applied. Depending on the concentration of the spray liquor, the amount of water used was between 1.000 and 2.000 l/ha. After three weeks, the degree of damage to the plants was determined and characterised by the values 0–5, which had the following meaning:

0   no effect
1   a few slightly burnt spots
2   marked damage to leaves
3   some leaves and parts of stalks partially dead
4   plant partially destroyed
5   plant completely dead.

The active compound, amounts used and resuls can be seen from the table which follows (page 36).

EXAMPLE B

Pre-emergence-test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterised by the values 0-5, which had the following meaning:

0 no effect
1 slight damage or delay in growth
2 marked damage or inhibition of growth
3 heavy damage and only deficient development or only 50 percent emerged
4 plants partially destroyed after germination or only 25 percent emerged
5 plants completely dead or not emerged.

The active compounds, the amounts applied and the results obtained can be seen from the following table:

Table

| Active compound | Amount of active compound used kg/ha | Post-emergence-test | | | | | | | | | | |
|---|---|---|---|---|---|---|---|---|---|---|---|---|
| | | Echino-chloa | Cheno-podium | Sina-pis | Ga-lin-soga | Stel-laria | Matri-caria | Carrots | Oats | Cotton | Wheat | Beans |
| | 1 | 4-5 | 5 | 5 | 5 | 5 | 5 | 5 | 4-5 | 5 | 5 | 5 |
| | 0,5 | 4 | 5 | 5 | 5 | 4 | 4 | 5 | 4 | 5 | 5 | 4 |

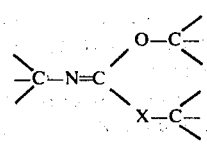

(D)

| Active compound | Amount of active compound used kg/ha | Pre-emergence-test | | | | | | | | | | |
|---|---|---|---|---|---|---|---|---|---|---|---|---|
| | | Echino-chloa | Cheno-podium | Sina-pis | Lo-lium | Stel-laria | Galin-soga | Matri-caria | Avena fatua | Cotton | Wheat | Buck-wheat | Maize (corn) |
| (D) | 5 | 5 | 5 | 5 | 5 | 5 | 5 | 5 | 4-5 | 3 | 5 | 3 |
| | 2,5 | 5 | 5 | 5 | 5 | 5 | 5 | 5 | 4 | 3 | 4-5 | 2 |

What is claimed is:

1. A process for the production of an N-chloroformyl carbamic acid amide or ester having the functional group

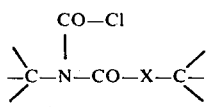

wherein X is oxygen, sulfur or

which comprises reacting an imino compound having the functional group

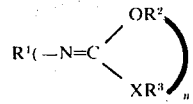

and free of interfering radicals with at least about 1 mole of phosgene per mole of imino group.

2. A process according to claim 1 in which the imino compound has the formula $$R^1(-N=C\begin{matrix}OR^2\\XR^3\end{matrix})_n \quad (I)$$

in which
R¹ is a monovalent or divalent optionally substituted aliphatic, cycloaliphatic, araliphatic or aromatic radical,
R² is an optionally substituted alkyl or aralkyl radical,
R³ is a monovalent optionally substituted aliphatic, cycloaliphatic, araliphatic or aromatic radical, and any two of the radicals R¹, R² and R³ can conjointly be a constituent of a 4-membered to 7-membered heterocyclic ring,
X is oxygen, sulfur or an N-R⁴ radical, in which
R⁴ is an optionally substituted C₁-C₆ alkyl, cycloalkyl, aralkyl or aromatic radical, or R³ and R⁴ together optionally form a constituent of a 4-membered to 7-membered ring, and
n is 1 when R¹ is monovalent and 2 when R¹ is divalent,
and the reaction is effected at a temperature of about −20°C to +200°C.

3. A process according to claim 2, in which R¹ is optionally substituted alkyl, alkenyl, alkylene or alkenylene with up to about 22 carbon atoms, optionally substituted cycloalkyl, cycloalkenyl, cycloalkylene or cycloalkenylene with about 4 to 10 carbon atoms, an optionally substituted araliphatic radical with 1 to about 4 carbon atoms in the aliphatic chain and naphthyl or phenyl as the aromatic moiety, or an optionally substituted aromatic radical with up to about 14 carbon atoms in the ring system, two or more aromatic radicals being possibly linked through C-C bonds or bridge members; R² is optionally substituted alkyl with up to about 22 carbon atoms, or optionally substituted aralkyl with 1 to about 4 carbon atoms in the alkyl moiety and naphthyl or phenyl as the aromatic moiety; R³ is optionally substituted alkyl or alkenyl with up to about 22 carbon atoms, optionally substituted cycloalkyl or cycloalkenyl with about 4 to 10 carbon atoms, optionally substituted araliphatic with 1 to about 4 carbon atoms in the aliphatic moiety and naphthyl or phenyl as the aromatic moiety, or an optionally substituted aromatic radical with up to about 14 carbon atoms in the ring system, two or more aromatic radicals being possibly linked through C—C bonds or via bridging members; and R⁴ is alkyl with 1 to about 4 carbon atoms, cycloalkyl with 5 or 6 carbon atoms, benzyl or phenyl.

4. A process according to claim 2, in which R¹ is optionally substituted alkyl, alkenyl, alkylene or alkenylene with up to about 8 carbon atoms, optionally substituted cycloalkyl, cycloalkenyl, cycloalkylene or cycloalkenylene with 5 or 6 carbon atoms, optionally substituted benzyl or phenethyl, or optionally substituted naphthyl, naphthylene, phenyl or phenylene; R² is optionally substituted alkyl with up to about 8 carbon atoms or optionally substituted benzyl or phenethyl; and R³ is optionally substituted alkyl or alkenyl with up to about 8 carbon atoms, optionally substituted cycloalkyl or cycloalkenyl with 5 or 6 carbon atoms, optionally substituted benzyl or phenethyl, or optionally substituted naphthyl or phenyl.

5. A process according to claim 2 in which at least one of R¹, R², R³ and R⁴ carries at least one substituent selected from the group consisting of alkyl of up to about 4 carbon atoms, halogen, nitrile, nitro, or alkoxy, alkylmercapto or alkylsulfonyl with up to about 4 carbon atoms, aryloxy, arylmercapto, alkoxy carbonyl with up to about 6 carbon atoms in the alkoxy radical, aryloxycarbonyl, acyloxy with up to about 6 carbon atoms, benzolyoxy, or arylsulfonyl.

6. A process according to claim 2 in which the reaction is effected with about 1.1 to 2 moles of phosgene per mole of imino group at about −10° to 150°C in the presence of at least one inert solvent selected from the group consisting of hydrocarbons, halogenated hydrocarbons, nitro-hydrocarbons, ethers or esters.

7. A process according to claim 1 wherein such N-chloroformyl carbamic acid or ester is selected from the group consisting of:

N-chloroformyl-N-phenyl-carbamic acid butylthiol ester,
N-chloroformyl-N-phenyl-carbamic acid phenylthiol ester,
N-chloroformyl-N-(3,4-dichlorophenyl)-carbamic acid methyl ester,
N-chloroformyl-N-phenyl-carbamic acid β-chloroethyl(thiol) ester,
N-chloroformyl-N-vinyl-carbamic acid methyl ester,
N-chloroformyl-N-(cis- or trans-β-chloro-vinyl)-carbamic acid methyl ester,
N-chloroformyl-N-phenyl-N',N'-pentyleneurea, and
N-chloroformyl-N-phenyl-N'-(β-chloroethyl)-N'-methylurea.

8. A process according to claim 1 wherein the imino compound has the formula

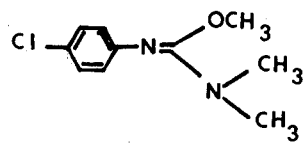

and the product has the formula

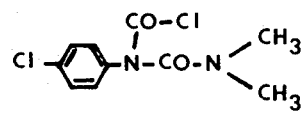

* * * * *